United States Patent
Santilli

(12) United States Patent Santilli
(10) Patent No.: US 6,383,134 B1
(45) Date of Patent: May 7, 2002

(54) SURGICAL STABILIZER HAVING SUCTION CAPABILITY

(76) Inventor: Albert N. Santilli, 28326 Gates Mill Blvd., Pepper Pike, OH (US) 44124

( * ) Notice: Subject to any disclaimer, the term of this patent is extended or adjusted under 35 U.S.C. 154(b) by 0 days.

(21) Appl. No.: 09/527,406

(22) Filed: Mar. 16, 2000

Related U.S. Application Data

(63) Continuation-in-part of application No. 09/420,164, filed on Oct. 18, 1999, which is a continuation of application No. 09/049,597, filed on Mar. 27, 1998, now Pat. No. 5,967,972

(60) Provisional application No. 60/042,472, filed on Mar. 28, 1997.

(51) Int. Cl.[7] .............................................. A61B 1/32
(52) U.S. Cl. ....................... 600/205; 600/210; 600/217; 600/219; 600/228; 600/229; 600/235
(58) Field of Search ................................. 600/201, 205, 600/210, 217, 219, 227, 228, 229, 231, 232, 233, 235, 37

(56) References Cited

U.S. PATENT DOCUMENTS

| | | |
|---|---|---|
| 4,366,819 A | 1/1983 | Kaster |
| 4,368,736 A | 1/1983 | Kaster |
| 5,727,569 A | 3/1998 | Benetti et al. |
| 5,836,311 A | 11/1998 | Borst et al. |
| 5,865,730 A | 2/1999 | Fox et al. |
| 5,885,271 A | 3/1999 | Hamilton et al. |
| 5,891,017 A | 4/1999 | Swindle et al. |
| 5,894,843 A * | 4/1999 | Benetti et al. ............... 128/898 |
| 5,967,972 A * | 10/1999 | Santilli et al. ............... 600/232 |
| 6,056,689 A * | 5/2000 | Lenox et al. ........... 600/210 X |
| 2001/0023311 A1 * | 9/2001 | Snow .......................... 600/37 |

* cited by examiner

Primary Examiner—Jeffrey A. Smith
(74) Attorney, Agent, or Firm—Rankin, Hill, Porter & Clark LLP

(57) ABSTRACT

A surgical stabilizer especially adapted for use in cardiac surgery includes first and second hollow legs that are disposed generally parallel to each other, each leg having a closed end and an open end. Each leg has an upper surface and a lower surface, the lower surface including a plurality of openings that are disposed adjacent each other. A yoke extends between and connects the first and second legs. A manifold is connected to the open end of each leg. When a suction tube is connected to the manifold, a vacuum can be applied to the openings in the legs so as to attract the surface of the heart to the legs. An adjustable embodiment of the invention includes first and second support arms that are connected to first and second legs. The support arms are connected pivotally to each other to permit the legs to be moved toward or away from each other. The legs can be provided with small pins, sharpened edges, and/or suction in order to engage or grasp the heart.

13 Claims, 3 Drawing Sheets

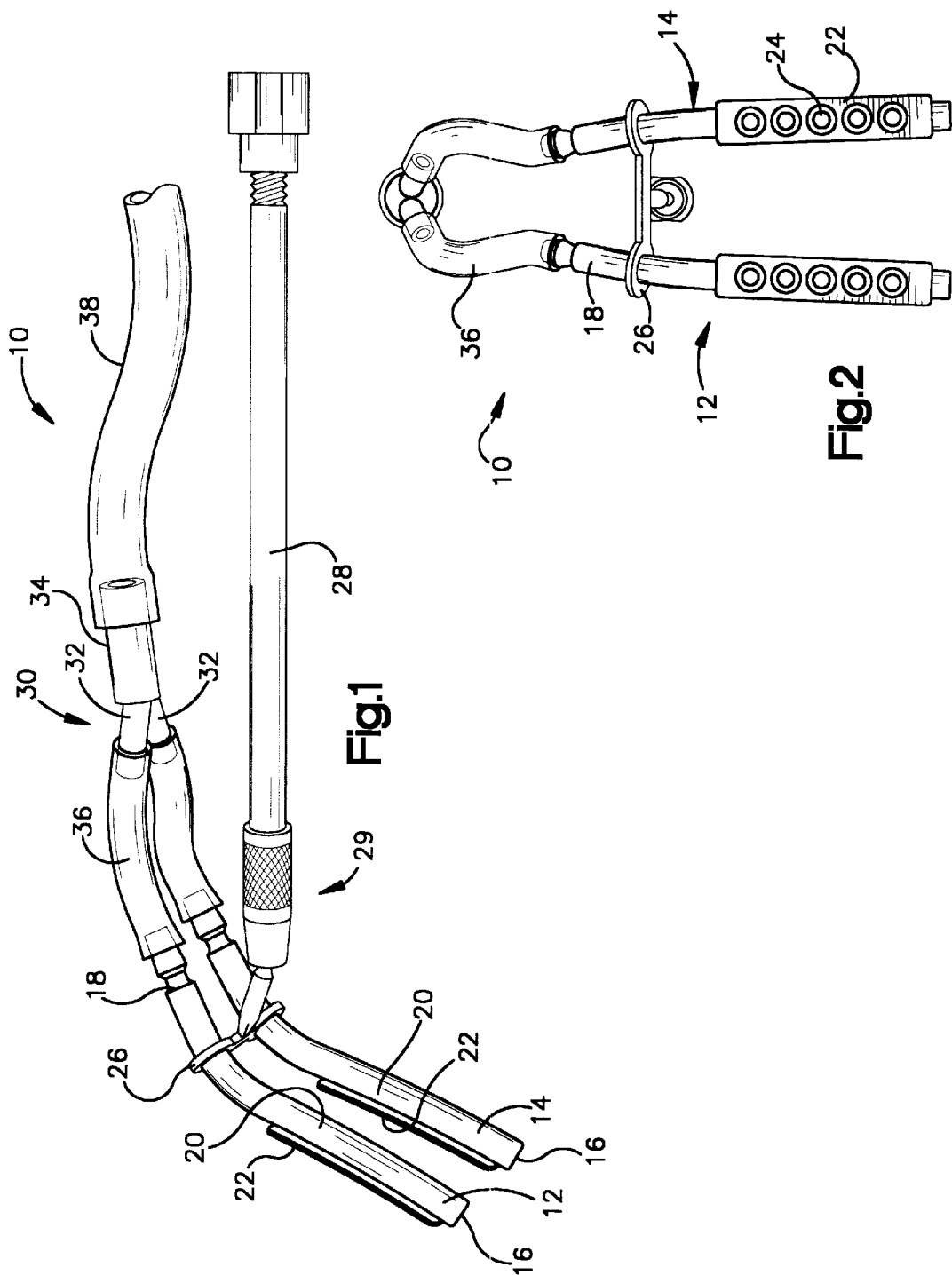

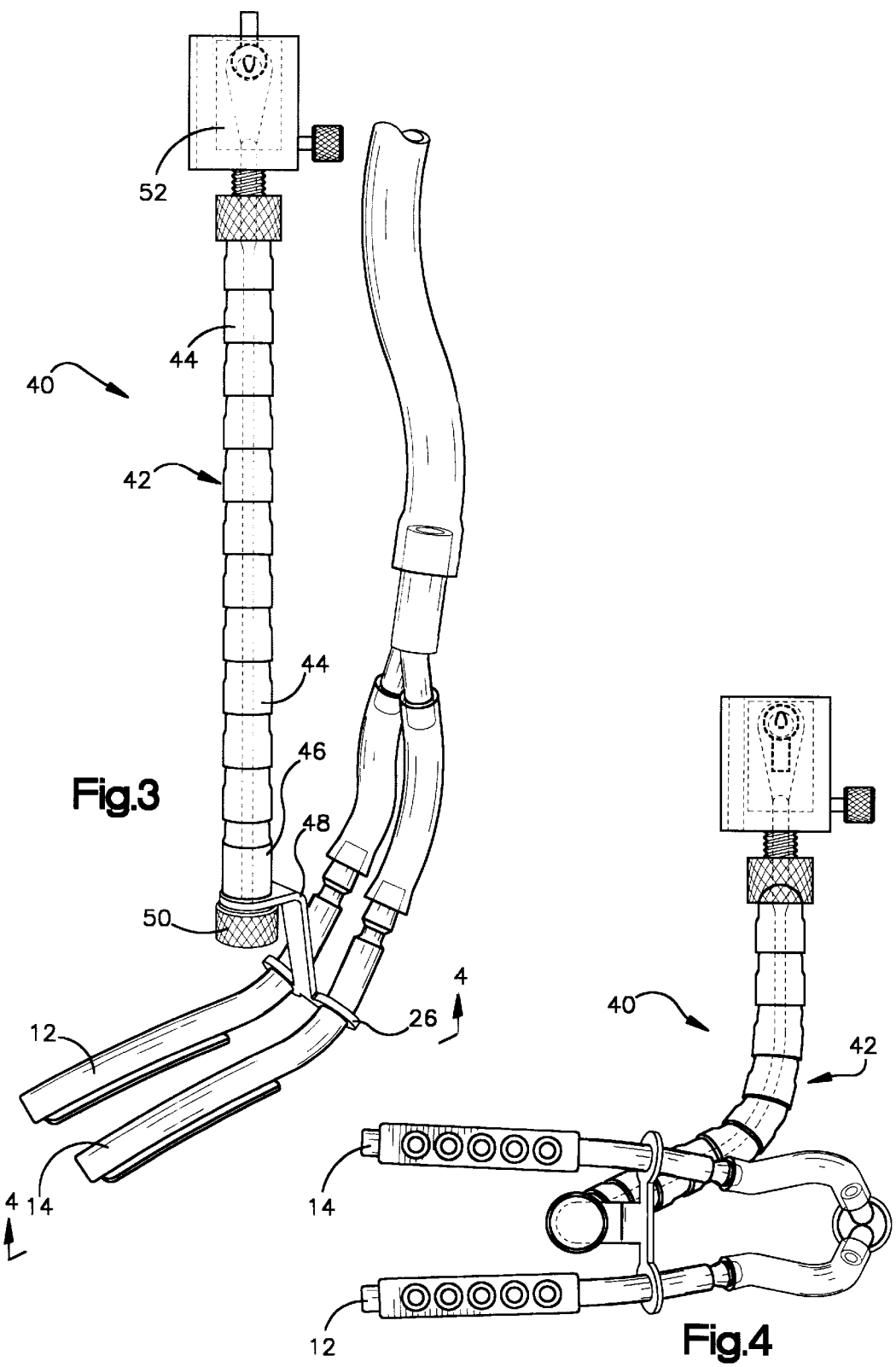

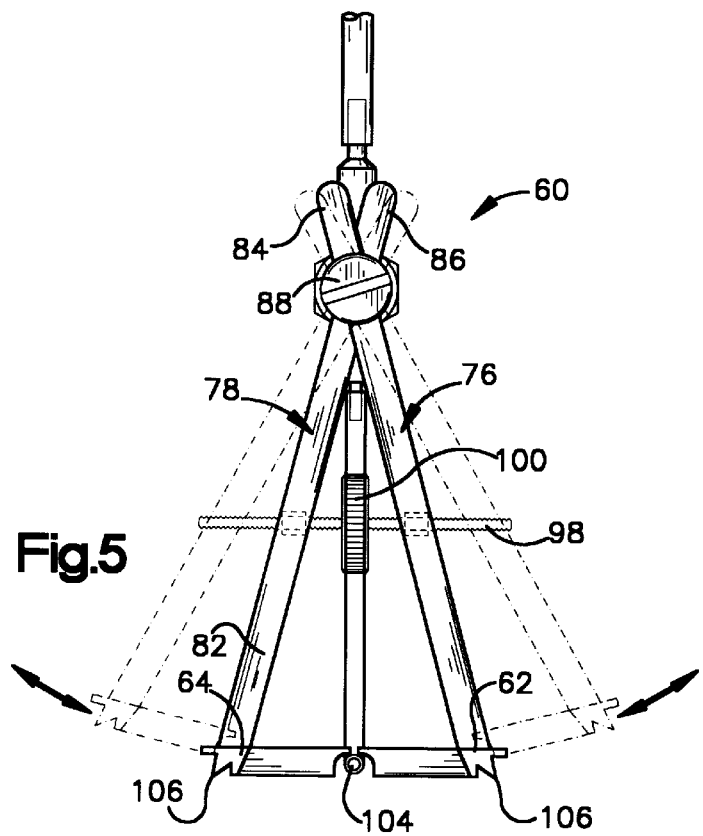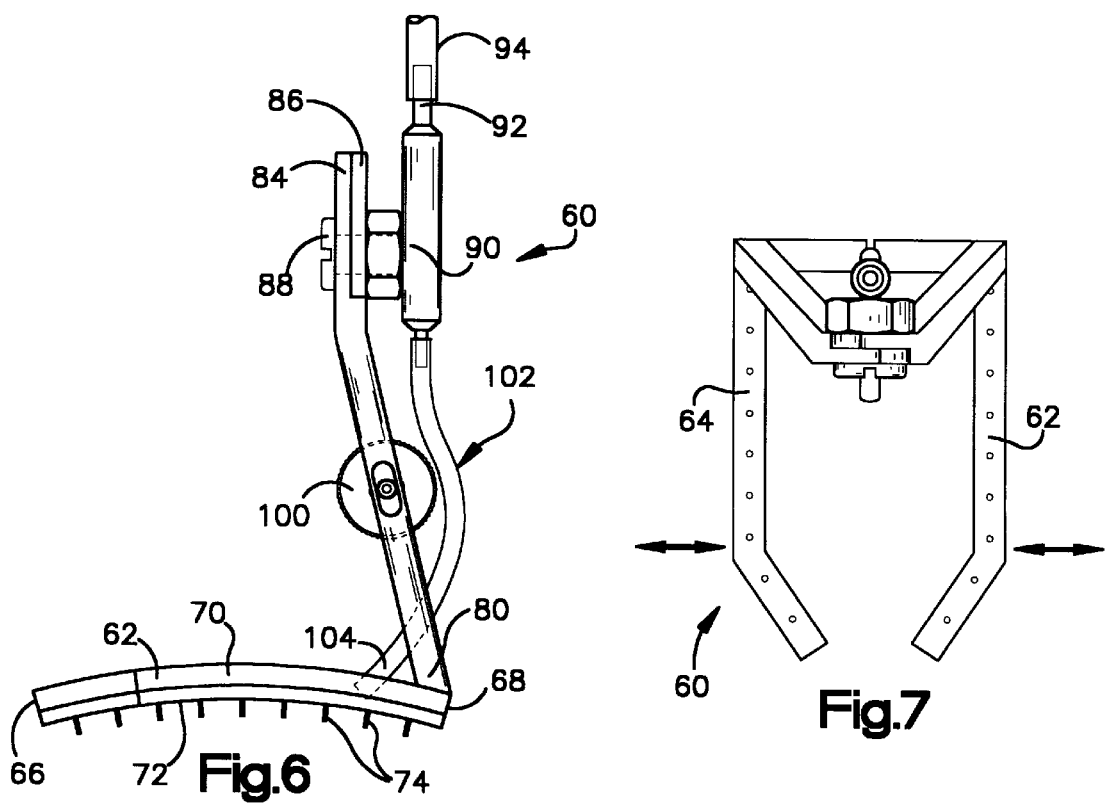

SURGICAL STABILIZER HAVING SUCTION CAPABILITY

REFERENCE TO RELATED PATENTS

The present invention is a continuation-in-part of U.S. application Ser. No. 09/420,164, filed Oct. 18, 1999 (pending) by Albert N. Santilli, which is a continuation of Ser. No. 09/049,597, filed Mar. 27, 1998, now U.S. Pat. No. 5,967,972, issued Oct. 19, 1999 to Albert N. Santilli, et al, which claimed priority based on U.S. Provisional Application No. 60/042,472, filed Mar. 28, 1997. The present application incorporates by reference the disclosure of each of the referenced documents and claims priority therefrom.

BACKGROUND OF THE INVENTION

1. Field of the Invention

The invention relates to surgical stabilizers of the type used in cardiac surgery and, more particularly, to a surgical stabilizer having suction capability.

2. Description of the Prior Art

In the course of a cardiac procedure such as bypass surgery that is performed while the heart is beating, it is necessary to greatly reduce the movement of the surface of the heart so that repairs or grafts can be made. It has been known to compress the surface of the heart by means of spaced, generally parallel legs that are attached to the end of an elongate handle. The handle is adjustably connected to a non-movable structure such as a cardiovascular retractor. By applying pressure to the surface of the heart, the region of the heart between the legs will be compressed and relatively starved for blood, thereby permitting surgery to be performed without the need for a heart-lung machine to stop the heart. Moreover, the compression applied by the stabilizer renders the portion of the heart between the legs relatively motionless so that grafts can be made.

A problem not addressed by prior stabilizers is that of applying just the right amount of compressive force to the surface of the heart so that movement of the surface of the heart is prevented while harm to the heart is avoided. Also, although certain prior devices have had adjustable components, the adjustment capability has been less than desired. Further, with respect to both cardiac surgery and other types of surgery, prior devices have not had the capability to engage or grasp tissue and spread it apart for purposes of conducting a surgical procedure.

Desirably, a surgical stabilizer would be available that would be able to adequately stabilize the surface of the heart while applying minimal compressive force. Further, such a stabilizer would be fully adjustable. Preferably, such a stabilizer would be able to engage or grasp tissue and spread it apart as may be necessary to perform a desired surgical procedure.

SUMMARY OF THE INVENTION

In response to the foregoing concerns, the present invention provides a new and improved surgical retractor that is provided with a means to engage or grasp tissue. The retractor according to the invention is intended for use in various types of surgical procedures, although it is especially effective in cardiac surgery. In one embodiment, the stabilizer includes legs through which suction can be applied through the lower surfaces thereof. The suction enables the surface of the heart to be grasped by the stabilizer, thereby minimizing the amount of compressive force required to stabilize the heart properly. In another embodiment, the legs are adjustable toward or away from each other and have lower surfaces with small pins or sharp edges that can engage tissue and move it apart. This embodiment of the invention also can be provided with hollow legs to which suction can applied.

A non-adjustable embodiment of the stabilizer according to the invention includes first and second hollow legs that are disposed generally parallel to each other, each leg having a closed end and an open end. Each leg has an upper surface and a lower surface, the lower surface including a plurality of openings which are disposed adjacent each other. This embodiment of the invention also includes a yoke extending between and connecting the first and second legs, and a manifold connected to the open end of each leg. When a suction tube is connected to the manifold, a vacuum can be applied to the openings in the legs so as to attract the surface of the heart to the legs.

An adjustable stabilizer according to the invention includes first and legs disposed generally parallel with each other, each leg having a distal end and a proximal end, and an upper surface and a lower surface. The stabilizer also includes first and second support arms each having a first end and a second end, the first end of the first support arm being connected to the first leg and the first end of the second support arm being connected to the second leg, each support arm being connected to its respective leg at or adjacent the proximal end thereof, the first and second arms being disposed approximately at a right angle to the first and second legs, respectively. The stabilizer further includes means for connecting the second ends of the first and second support arms to each other and for permitting the support arms to be pivoted relative to each other; as Nell as a handle to which the means for supporting the second ends is connected. The stabilizer can be provided with means for engaging or grasping the surface of the heart, such as small pins, sharpened edges, and/or suction.

The foregoing features and advantages will be apparent from the accompanying drawings and description that follow.

BRIEF DESCRIPTION OF THE DRAWINGS

FIG. 1 is a perspective view of a surgical retractor according to the invention in which a suction capability is provided;

FIG. 2 is a bottom plan view of the retractor of FIG. 1;

FIG. 3 is a side elevation view of the retractor of FIG. 1, with a gooseneck-type adjustable handle;

FIG. 4 is a bottom plan view of the retractor of FIG. 3;

FIG. 5 is a front elevation view of a surgical retractor according to the invention in which adjustable legs are provided;

FIG. 6 is a side elevation view of the retractor of FIG. 5; and

FIG. 7 is a top plan view of the retractor of FIG. 5.

DESCRIPTION OF THE PREFERRED EMBODIMENT

Referring to FIGS. 1 and 2, a surgical stabilizer according to the invention is indicated generally by the reference numeral 10. The stabilizer 10 includes first and second hollow legs 12, 14 that are disposed generally parallel to each other. Each leg 12, 14 has a closed end 16 and an open end 18. Additionally, each leg 12, 14 has an upper surface 20 and a lower surface 22. The lower surface 22 has a plurality of openings 24 that are disposed adjacent to each other, in this instance in a straight line. The lower surface 20 can be formed by deforming the legs 12, 14 to provide a flat, elongate surface. Alternatively, as illustrated, the legs 12, 14 can be open on the underside, and an elongate plate having openings 24 can be secured thereto as by soldering.

A yoke 26 extends between and connects the first and second legs 12, 14. Preferably the connection is made toward the open end 18. The yoke 26 is attached to a handle 28 that in turn is connected to a stable object such as a cardiovascular retractor (not shown). The yoke 26 and the handle 28 are connected to each other by a ball and socket connection indicated by the reference numeral 29 that permits the yoke 26 to be adjusted relative to the handle 28. A manifold 30 is connected to the open end 18 of each leg 12, 14. The manifold 30 is a Y-shaped member having hollow branched legs 32 and a hollow stem 34. Flexible tubes 36 connect the open ends 18 and the branched legs 32. An elongate, flexible tube 38 is connected to the stem 34. The tube 38 is connected at its other end to a vacuum source (not shown). As will be apparent from the Figures, when a vacuum is applied through the tube 38, suction will be created within the openings 24.

Referring now to FIGS. 3 and 4, an alternative embodiment of the invention is indicated by the reference numeral 40. The stabilizer 40 utilizes the legs 12, 14, the yoke 26, and the manifold 30 and associated tubing from the stabilizer 10. However, the yoke 26 is connected to a gooseneck type of handle 42. The handle 42 is disclosed in application Ser. No. 09/420,164 (pending). The handle 42 is comprised of a series of tubular members 44 through which a cable (not shown) extends. The cable is connected to a fitting 46, which in turn is connected to the yoke 26 by means of a malleable neck 48 and a threaded pin 50. The other end of the cable is connected to a formation (not shown) that is disposed within a housing 52. The housing 52 can be attached to a stable object such as a cardiovascular retractor. A cam (not shown) is disposed within the housing 52 and is operatively connected to the formation. A handle 54 is connected to the cam and projects from the housing 52. When the handle 54 is positioned such that the cam relaxes the cable, the tubular members 44 will be loosened, thereby permitting the position of the stabilizer 40 to be adjusted. Thereafter, the handle 54 can be moved so that the cam is actuated to tighten the cable, which in turn will compress the tubular members 44. The handle 40 thus will be locked into the position that has been selected by the surgeon.

Referring now to FIGS. 5–7, another embodiment of the stabilizer according to the invention is indicated generally by the reference numeral 60. The stabilizer 60 includes first and second legs 62, 64 that are disposed generally parallel to each other and lie in a common plane. Each leg 62, 64 has a distal end 66 and a proximal end 68. Additionally, each leg 62, 64 has an upper surface 70 and a lower surface 72. The lower surface 72 has a plurality of small pins 74 (FIG. 6) that are disposed adjacent to each other, in this instance in a straight line.

The stabilizer 60 includes first and second support arms 76, 78. The first end 80 of the first support arm 76 is connected to the first leg 62 near the proximal end thereof, while the first end 82 of the second support arm 78 is connected to the second leg 64 near the proximal end thereof. The support arms 76, 78 are disposed approximately at a right angle to the plane in which the first and second legs 62, 64 lie.

The first and second arms 76, 78 have second ends 84, 86, respectively. The second ends 84, 86 each include an opening through which a screw 88 extends. The screw 88 is connected to a formation 90 that is attached to the end of a malleable neck 92 which, in turn, is attached to the end of a handle 94. The arms 76, 78 are compressed by the screw 138. Each of the arms 76, 78 includes a threaded opening at a location intermediate the first and second ends 80 and 84 and 82 and 86, respectively. The threaded openings are oriented generally perpendicular to the legs 62, 64. A threaded stud 98 extends through the threaded openings. The stud 98 has a knurled wheel 100 mounted thereon. The threads in the threaded openings and the threads on the stud 98 are formed so that rotation of the knurled wheel 100 in one direction will cause the support arms 62, 64 to move toward each other and rotation of the knurled wheel 100 in the other direction will cause the support arms 62, 64 to move away from each other.

A rigid tube 102 extends from the bottom of the formation 90 and has an open end 104 that is disposed approximately in the plane in which the lower surfaces 72 lie. Because the formation 90, the neck 92, and the handle 94 are hollow, suction can be applied through the tube. If desired, gas such as carbon dioxide can be blown outwardly through the opening 104.

Referring now to FIG. 5, the legs 62, 64 optionally can be provided on the lower surface with a plurality of sharp edges 106 that are parallel to the legs 62, 64. As with the pins 74 shown in FIG. 6, the edges 106 are designed to engage tissue and spread it when the legs 62, 64 are moved apart.

Referring to FIG. 7, an alternative embodiment of the legs 62, 64 is shown. In this embodiment, the distal ends 66 and the proximal ends 68 are toed-in toward each other. This configuration of the legs 62, 64 creates a more closed work area in which to perform surgical operations.

If desired, the stabilizer 60 can be provided with legs 12, 14 that are used with the stabilizer 10. In this instance, a pair of flexible tubes (not shown) extend from the formation 90 and are connected to the open ends 18. Optionally, the lower surfaces 22 can be provided with pins 74 or sharp edges 106. Accordingly, the stabilizer 60 not only is adjustable, but the legs thereof can be provided with a suction capability and/or a capability to engage tissue mechanically.

As will be appreciated from the foregoing description, the stabilizer according to the invention can apply suction to the lower surfaces 22 of the legs 12, 14 in an effective manner. The alternative embodiments of the invention enable the stabilizer to be adjusted readily and to engage tissue so that it can be spread apart as may be necessary.

Although the invention has been described in its preferred form with a certain degree of particularity, it will be understood that the present disclosure of the preferred embodiment has been made only by way of example and that various changes may be resorted to without departing from the true spirit and scope of the invention as hereinafter claimed. It is intended that the patent shall cover, by suitable expression in the appended claims, whatever degree of patentable novelty exists in the invention disclosed.

What is claimed is:

1. A stabilizer especially adapted for use in cardiac surgery, comprising:

first and second hollow legs disposed generally parallel to each other, each leg having a closed end and an open end, each leg having an upper surface and a lower surface, the lower surface including a plurality of openings, the openings being disposed adjacent each other;

a yoke extending between and connecting the first and second legs such that the legs cannot move relative to each other, the yoke being in the form of a cross-bar through which the legs extend and to which the legs are rigidly connected; and a manifold connected to the open end of each leg.

2. The stabilizer of claim 1, further comprising a suction tube connected to the manifold.

3. The stabilizer of claim 1, wherein the openings are disposed adjacent the closed end of the legs.

4. The stabilizer of claim 1, wherein the lower surfaces of the legs are flat and elongate.

5. The stabilizer of claim 1, wherein the lower surfaces of the legs are defined by elongate openings to which elongate plates having openings therein are secured.

6. A stabilizer especially adapted for use in cardiac surgery, comprising:

first and second legs disposed generally parallel to each other, each leg having a distal end and a proximal end, and an upper surface and a lower surface, each of the legs being hollow and including a plurality of openings on the lower surfaces thereof;

a suction tube connected to each of the legs;

first and second support arms each having a first end and a second end, the first end of the first support arm being connected to the first leg and the first end of the second support arm being connected to the second leg, each support arm being connected to its respective leg at or adjacent the proximal end thereof, the first and second arms being disposed approximately at a right angle to the first and second legs, respectively;

means for connecting the second ends of the first and second support arms to each other and for permitting the support arms to be pivoted relative to each other, the means for connecting including:

a formation;

an opening in the second end of each support arm; and a fastener extending through the openings in the support arms, the fastener being connected to the formation;

threaded openings formed in the support arms at a location intermediate the first and second ends, the threaded openings beings oriented generally perpendicular to the legs;

a threaded stud extending through the threaded openings, the stud having a knurled wheel mounted thereon, the threads in the threaded openings and the threads on the stud being formed so that rotation of the knurled wheel in one direction will cause the support arms to move toward each other and rotation of the knurled wheel in the other direction will cause the support arms to move away from each other;

a handle to which the means for connecting the second ends is connected.

7. The stabilizer of claim 6, wherein the fastener is a screw.

8. The stabilizer of claim 6, further comprising a plurality of pins projecting from the lower surfaces of the first and second legs.

9. The stabilizer of claim 6, further comprising a plurality of sharpened edges included as part of the lower surfaces of the first and second legs.

10. The stabilizer of claim 6, wherein the distal and proximal ends of the legs are angled toward each other.

11. The stabilizer of claim 6, wherein the handle is hollow, and the suction tubes are connected at one end to their respective legs and are connected at the other end to the handle.

12. The stabilizer of claim 6, wherein the lower surfaces of the leg are flat and elongate.

13. The stabilizer of claim 6, wherein the lower surfaces of the legs are defined by elongate openings to which elongate plates having openings therein are secured.

* * * * *